United States Patent [19]
Cleland

[11] 4,434,372
[45] Feb. 28, 1984

[54] METHOD AND APPARATUS FOR WIDE ANGLE BEAM SCANNING TO INTERNALLY IRRADIATE HOLLOW OBJECTS

[75] Inventor: Marshall Cleland, Huntington Station, N.Y.

[73] Assignee: Radiation Dynamics, Inc., Melville, N.Y.

[21] Appl. No.: 340,915

[22] Filed: Jan. 20, 1982

[51] Int. Cl.³ .................... G01K 1/08; H01J 3/14
[52] U.S. Cl. .................................................. 250/400
[58] Field of Search ............... 250/400, 492.3, 398

[56] References Cited

U.S. PATENT DOCUMENTS 3,174,084  3/1965  Westendorp et al. ............. 335/210
3,632,398  1/1972  Konig ................................ 427/43.1

FOREIGN PATENT DOCUMENTS

2201523  4/1974  France ............................. 250/492.3

Primary Examiner—Alfred E. Smith
Assistant Examiner—Constantine Hannaher
Attorney, Agent, or Firm—Howard L. Rose

[57] ABSTRACT

Method and apparatus for wide angle beam scanning to internally irradiate hollow objects with a beam of charged particles utilizes a scanning deflection device to scan the beam within the object to be irradiated through an angle of deflection greater than 90° from the axis along which the beam is received by the scanning deflection device. The object to be irradiated can be rotated about the scanning deflection device or the scanning deflection device can be rotated to circumferentially irradiate the object, and the object is translated relative to the scanning deflection device to irradiate an entire object, such as a tube, a container having a closed end or an object having a toroidal configuration, such as a pneumatic tire.

20 Claims, 17 Drawing Figures

METHOD AND APPARATUS FOR WIDE ANGLE BEAM SCANNING TO INTERNALLY IRRADIATE HOLLOW OBJECTS

BACKGROUND OF THE INVENTION

1. Field of the Invention

The present invention pertains to the internal irradiation of hollow objects with a beam of charged particles and, more particularly, to a method and apparatus for effecting such irradiation with wide angle beam scanning deflection within the object to be irradiated.

2. Discussion of the Prior Art

Beams of charged particles are commonly used to irradiate objects to alter material characteristics of the objects, such as by cross-linking, polymerizing, curing, sterilizing and the like.

Irradiation of flat or cylindrical objects with a beam of charged particles, such as electrons, is normally accomplished via external irradiation. That is, flat sheets or films of plastic, rubber or similar materials are normally irradiated from one or both sides, and insulated wire and hollow plastic tubing are normally irradiated from the outside with charged particles sufficiently energetic to penetrate entirely through the material of the object. For this type of external irradiation, conventional techniques of scanning the beam through a small deflection angle range, up to a maximum of about ±30°, are sufficient to achieve uniform radiation dosage. A problem exists, however, when utilizing conventional beam scanning devices to externally irradiate hollow objects, such as pipes, vessels, drums, balls, pneumatic tires and the like, with charged particles insufficiently energetic to penetrate the walls or shells of the objects in that the irradiation is not uniform and complete to achieve the desired results.

Accordingly, prior art beam scanning devices and techniques have had the disadvantages of not being effective to uniformly irradiate hollow objects externally because it is extremely important to assure uniform and complete irradiation of the entire internal surface of hollow objects in order to achieve the desired effect, particularly to cure or vulcanize the inner liner of pneumatic tires or to vulcanize the inner half of the body or tread of the tire. Prior art methods and apparatus for scanning beams of charged particles have had the disadvantages of having too narrow a scanning angle to permit even and thorough internal irradiation of hollow objects. U.S. Pat. No. 3,632,398 to Konig and British Pat. No. 717,549 to Siemens-Reiniger-Werke A.G. are representative of prior art irradiation of interior cavities.

SUMMARY OF THE INVENTION

Accordingly, it is a primary object of the present invention to overcome the above mentioned problems and disadvantages of the prior art by utilizing wide angle beam scanning to internally irradiate hollow objects with a beam of charged particles.

Another object of the present invention is to scan a beam of charged particles through an angle of deflection greater than 90° from an axis along which the beam is received by a scanning deflection device to permit wide angle scanning of the beam internally of a hollow object.

An additional object of the present invention is to internally irradiate hollow objects with a beam of charged particles by scanning the beam to define a plane of irradiation covering a circumferential swath around the object to be irradiated, and moving rotationally and translationally the beam scanning device or the object to evenly and thoroughly irradiate all internal surfaces of the object.

The present invention has a further object in that a device for deflecting a beam of charged particles over a wide angle internally of a hollow object to be irradiated is driven at an angular rate slower at portions corresponding to corners of the object to be irradiated to thereby evenly irradiate objects having varying configurations, such as closed end vessels, tanks and the like.

Some of the advantages of the present invention over the prior art are that the full inner circumference of a hollow object to be irradiated can be irradiated by disposing a wide angle beam scanning device within the object, objects of varying configurations that cannot be irradiated using conventional, small-angle beam scanning techniques can be irradiated using wide angle beam scanning in accordance with the present invention, and the wide angle beam scanning method and apparatus of the present invention provides even, uniform internal irradiation.

The present invention is generally characterized in a wide angle beam scanning apparatus for internally irradiating hollow objects with a beam of charged particles including a particle accelerator for producing a beam of charged particles and a scanning deflection device configured to be disposed within an object to be irradiated for receiving the beam along beam axis and deflecting the beam from the beam axis to scan the beam through an angle of deflection greater than 90° from the axis whereby the inner surface of the object can be irradiated with charged particles.

The present invention is further generally characterized in method of internally irradiating hollow objects with a beam of charged particles including the steps of disposing a beam scanning deflection device within an object to be irradiated, and operating the beam scanning deflection device to scan the beam over an angle relative to a beam axis along which the beam is received by the beam scanning deflection device to irradiate a swath of an object to be irradiated.

Other objects and advantages of the present invention will become apparent from the following description of the preferred embodiment taken in conjunction with the accompanying drawings.

DESCRIPTION OF THE PREFERRED EMBODIMENT

Figures 1, 2, 2A:
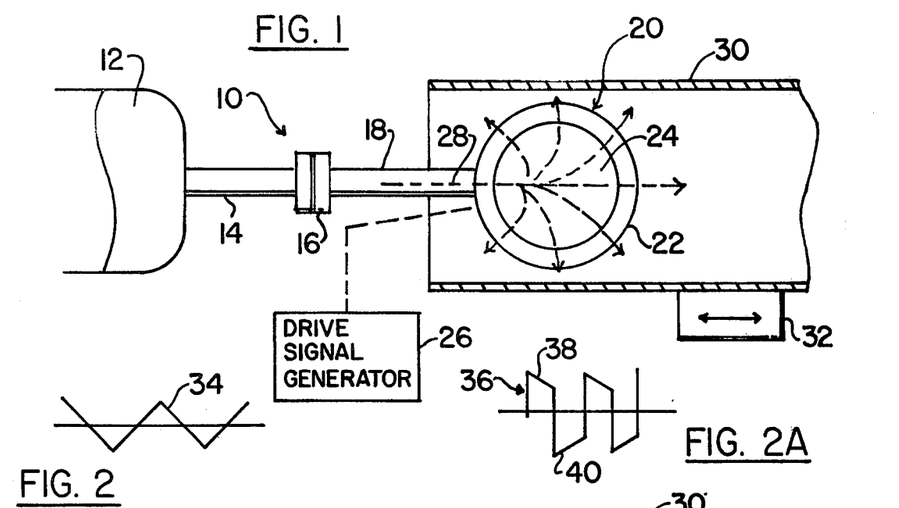
FIG. 1 is a diagrammatic view of wide angle beam scanning apparatus in accordance with the present invention for internally irradiating a hollow object.
FIGS. 2 and 2a illustrate drive signal waveforms for the scanning deflection device of the apparatus of FIG. 1.

Wide angle beam scanning apparatus 10 according to the present invention is illustrated in FIG. 1 and includes a particle accelerator 12, such as an electron beam accelerator, as described in U.S. Pat. No. 2,875,394 to Cleland, supplying a beam of charged particles via a vacuum pipe 14, a rotating joint 16 and a vacuum pipe 18 to a beam scanning deflection device 20 having a vacuum chamber 22 and a beam scanning magnet 24 receiving a drive signal from a generator 26 to control deflection of a beam of electrons received by the device 20 along an axis 28. An object to be irradiated 30, such as a hollow pipe or tube, is supported on a fixture 32, and the scanning deflection device 20 is rotatable within the object 30 while the object 30 is translated in a direction along the axis 28 by fixture 32 such that the length of the object can be irradiated while the scanning deflection device is rotated to irradiate a circumferential swath around the object.

A drive signal 34 for driving the scanning deflection device 20 is illustrated in FIG. 2 and has a sawtooth or preferably a triangular waveform such that for each cycle the beam is initially deflected an angle greater than 90° from the axis 28, preferably an angle of about 135°, and thereafter the beam is scanned through the axis 28 to terminate at an angle of 135° on the opposite side of the axis providing a 270° scan. The beam is then returned to the initial deflection position at the beginning of the next cycle. Accordingly, the drive signal 34 will scan the beam while the scanning deflection device 20 is rotated to irradiate a circumferential swath along the inner surface of the object 30, and the length of the object 30 is irradiated as the object is moved along the axis 28 by fixture 32.

A variation of a drive signal for driving scanning deflection device 20 is shown in FIG. 2a wherein each cycle of the drive signal 36 has positive and negative ramp portions 38 and 40, respectively, such that the beam is scanned from an initial deflection angle of 135° relative to the axis 28 to a deflection angle of 45° and then scanned from 135° to 45° on the opposite side of axis 28. In this manner, the irradiated circumferential swath is reduced in width with a resulting increase in efficiency due to elimination of the portion of the scan extending along the axis 28 within 45° on either side thereof.

Figure 3:
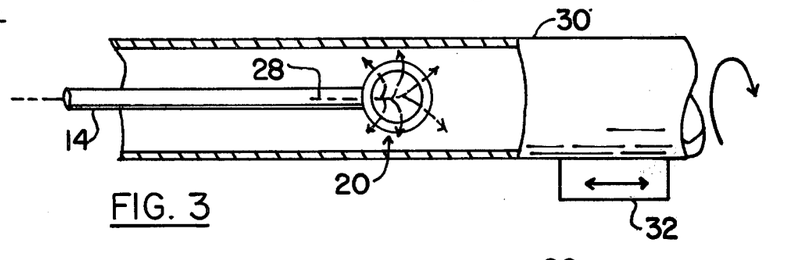
FIG. 3 is a diagrammatic view of a modification of the wide angle beam scanning apparatus of FIG. 1.
Figure 4:
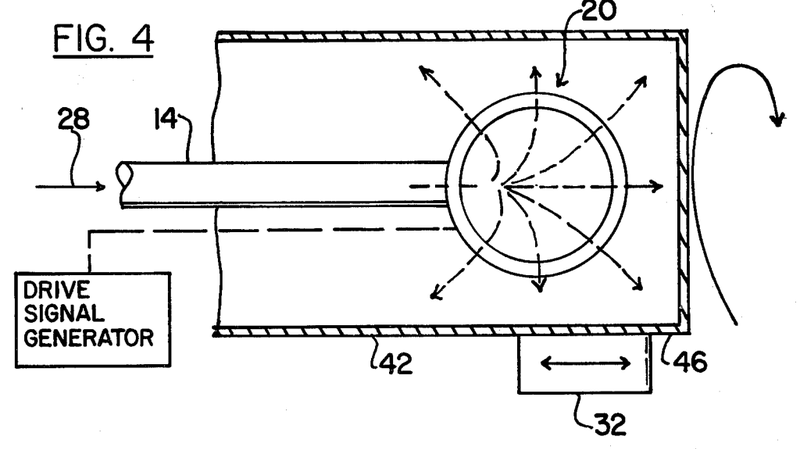
FIG. 4 is a diagrammatic view of the wide angle beam scanning apparatus of FIG. 3 utilized to irradiate a closed end object.
Figure 5:
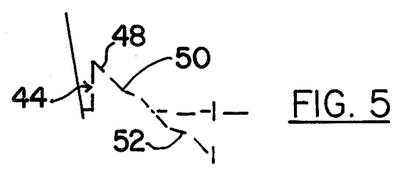
FIG. 5 illustrates a drive signal waveform for the scanning deflection device of the apparatus of FIG. 4.

In the modification of FIG. 3, the object 30 is rotated as well as longitudinally moved by fixture 32 such that the scanning deflection device 20 can be held stationary while the object is simultaneously rotated and translated coaxially along the beam axis 28. The structure of the modification of FIG. 3 is the same as that of FIG. 1 with the exception that joint 16 is not required and the vacuum pipe 14 can lead directly to the scanning deflection device 20. The drive signal waveforms of FIGS. 2 or 2a can be used to drive the scaning deflection device dependent upon the width of the circumferential irradiated swath desired.

Where the object to be irradiated has a relatively short length with a closed end, such as a drum-type container 42 as shown in FIG. 4, the beam scanning apparatus can be the same as that of FIG. 3 with the drive signal for the scanning deflection device 20 having a waveform 44 as shown in FIG. 5 producing a scan pattern modulated to provide a uniform radiation dosage over the entire inner surface of the container 42 including the "corner" regions 46 where the end and side walls of the container meet. To this end, the drive signal waveforms 34 or 36 of FIGS. 2 and 2a can be used to irradiate the inner surface of the side wall of the container as the container is translated along axis 28, and the drive signal waveform 44 is used for irradiation of the corner and end regions of the container. The drive signal waveform 44 has a general sawtooth or triangular configuration; however, the ramp 48 of the waveform is non-linear with shallow slope portions 50 and 52 positioned to cause the beam to dwell at the corner regions to cause more electrons to be deposited thereat. The shallow slope portions 50 and 52 distort waveform 44 from a linear or "triangular" sawtooth waveform and are required because, as the container rotates about the beam axis 28, the area of the annular end portions irradiated with electrons will increase in direct proportion to the displacement from the central axis such that the dwell time of the beam should increase as the deflection angle from the beam axis increases. Accordingly, the drive signal generator is programmed to drive the scanning deflection device to scan a circumferential swath, such as from 45° to 135° on opposite sides of the beam axis, and irradiate the cylindrical side wall during axial movement of the container; and, when the scanning deflection device has reached the deepest penetration, the drive signal generator is programmed to produce the drive signal waveform 44 to uniformly irradiate the end corner regions of the container. If desired, a drive signal waveform can be used to produce a scan of 0° to 45° on either side of the beam axis to irradiate the corner and end regions of the container, such a drive signal waveform having a sawtooth shape.

Figure 6:
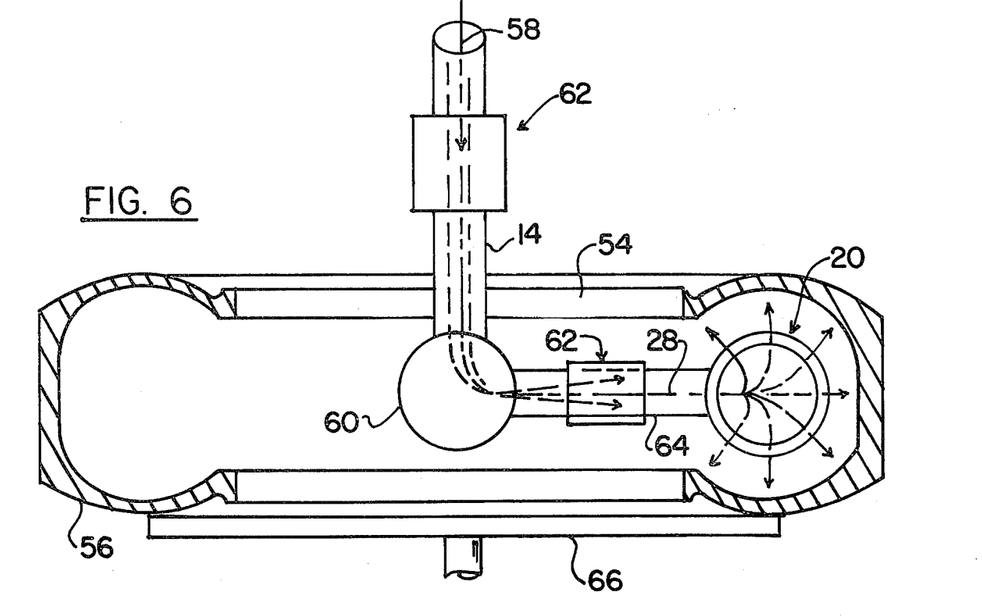
FIG. 6 is a diagrammatic view of an embodiment of the wide angle beam scanning apparatus of the present invention utilized for irradiating pneumatic tires.

Wide angle beam scanning apparatus 54 for irradiation of an object having a toroidal shape, such as a pneumatic tire 56, is shown in FIG. 6 and includes a vacuum pipe 14 supplying a beam of electrons 58 from an electron beam accelerator (not shown) to a beam deflection magnet 60 disposed along the central axis of the tire 56 and in a central plane through the tire, the magnet 60 deflecting the beam 58 by 90° to direct it via a vacuum pipe 64 to the scanning deflection device 20 along beam axis 28. Quadrupole lenses 62 may be used before and after the 90° deflection magnet to compensate for the asymetrical focus of the magnet so as to deliver a small-diameter electron beam to the scanning deflection device 20. The scanning deflection device 20 is disposed within the carcass of the tire 56, and the tire is supported on a rotating fixture 66 for rotating the tire about its axis.

In operation, the wide angle beam scanning apparatus 54 can be used to cure the inner liner of tire 56 by placing the tire on fixture 66 and positioning the tire to have the scanning deflection device 20 disposed therein. The scanning deflection device is desirably driven with a sawtooth or triangular waveform, such as waveform 34 of FIG. 2, such that the beam 58 received along axis 28 is scanned from an angle relative to the beam axis of 135° on one side of the axis to 135° on the opposite side of the axis while the tire is rotated about its axis by fixture 66. In this manner, the entire inner liner of the tire is irradiated by the wide angle beam scanning from scanning deflection device 20 coupled with the rotation of the tire.

Figure 7:
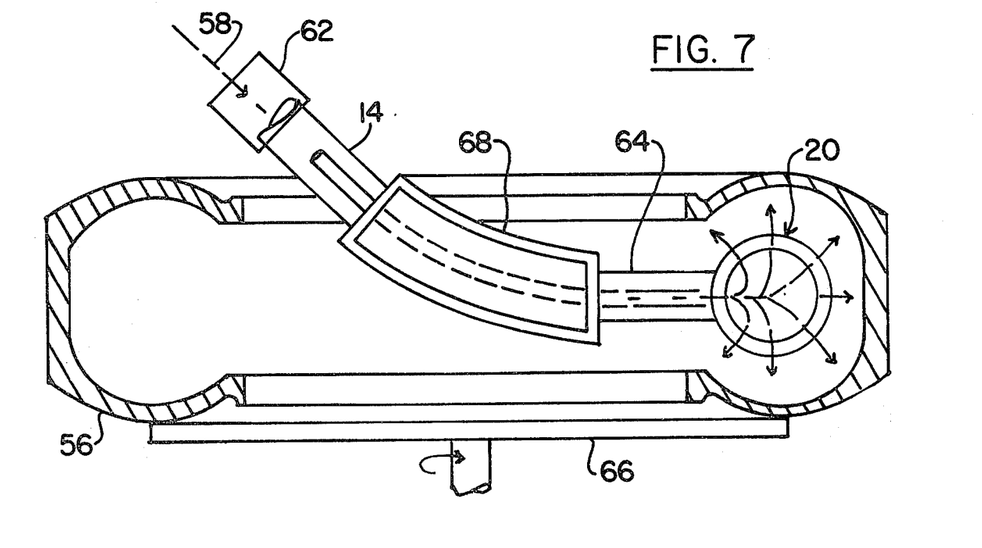
FIG. 7 is a diagrammatic view of a modification of the apparatus of FIG. 6.

A modification of the wide angle beam scanning apparatus of FIG. 6 is shown in FIG. 7 wherein the electron beam 58 is not supplied along an axis coinciding with the axis of rotation of the tire but rather is supplied at approximately an angle of 45° to the axis of rotation of the tire thereby having the advantage of requiring only a 45° deflection by a deflection magnet 68 disposed along the axis of rotation of the tire centrally of the tire. The reduced deflection angle of the deflection magnet coupled with elongating the pole tips thereof weakens the focal properties of the deflection magnet which is beneficial in accurately scanning the beam within the tire and supplying the beam to the scanning deflection device 20 via vacuum pipe 64. That is, the use of a 90° deflection magnet causes the beam to focus and diverge before reaching the scanning deflection device which can cause undesirable beam loss and bombardment of the scanning deflection device unless compensated by the quadrupole lenses. The 45° deflection magnet 68 has a much longer focal length thereby reducing the problems associated with a diverging beam. The drive signal waveform supplied to the scanning deflection device 20 is preferably the sawtooth or triangular waveform 34 of FIG. 2 such that the entire inner liner of the tire is irradiated as the tire is rotated.

Figure 8:
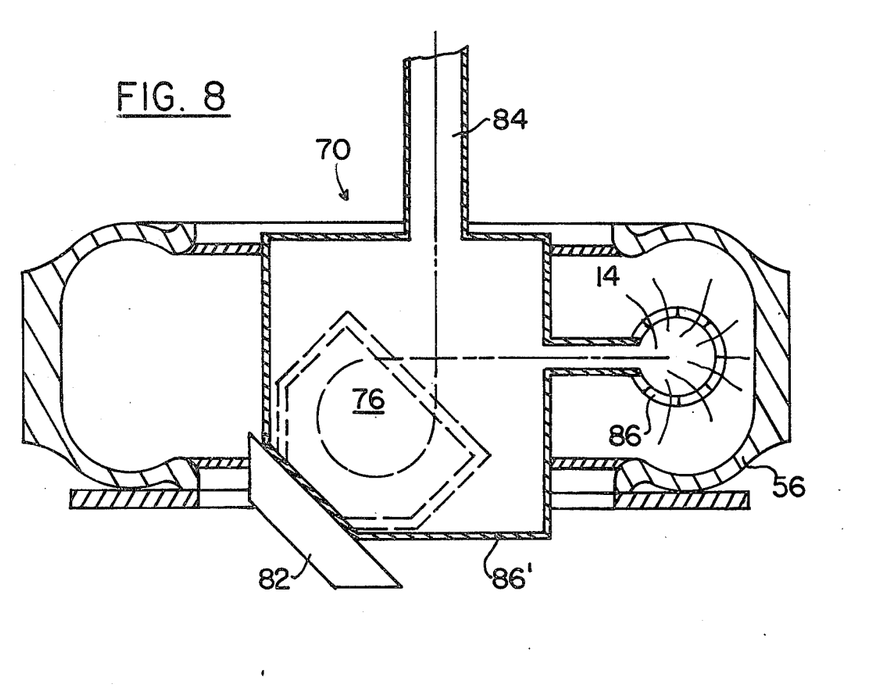
FIG. 8 is a diagrammatic side view partially in section of another apparatus for irradiating the interior of a tire carcass.
Figure 9:
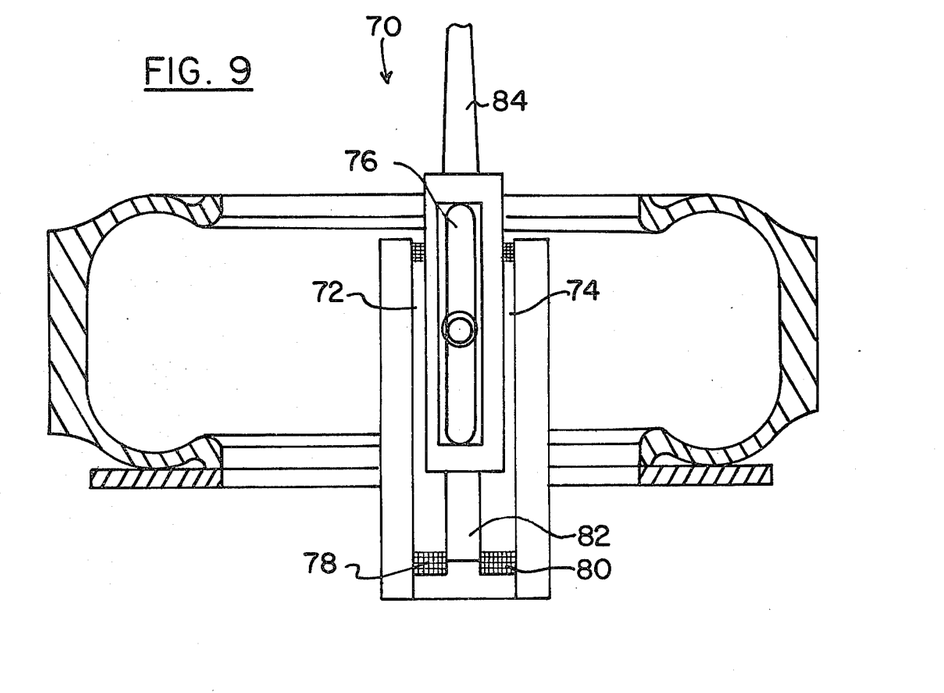
FIG. 9 is an end view of the apparatus of FIG. 8.

Another embodiment of the scanning apparatus of the present invention is illustrated in FIGS. 8 and 9 of the accompanying drawings. In this embodiment, the beam is again directed along the axis of the line 58 but is rotated 270° in a magnetic arrangement to be described.

A deflection magnet assembly 70, as illustrated in co-pending application Ser. No. 063,822 filed on Aug. 6, 1979 in the names of Thompson, et al. and assigned to the assignee of the present invention, may also be employed. The assembly includes a pair of magnetic pole pieces 72 and 74 positioned along opposite sides of a deflection chamber 76 and electrical windings 78 and 80 are wound around the pole pieces which are coupled with a magnetic flux return yoke 82. The magnetic pole pieces 72 and 74 are arranged at an angle of 45° to the central axis of the electron beam entering the assembly 70 via pipe 84 and leaving the assembly via pipe 14.

The assembly is located in an evacuated deflection chamber 86 that can be made of any non-magnetic metal, such as stainless steel; and, heavy gauge material can be used in the construction of the deflection chamber since the deflection field does not have any AC components. The deflection magnet assembly 70 can be made of solid iron or steel plates since the magnetic field is constant, the pole pieces 72 and 74 being preferably flat and arranged in parallel relation to produce a uniform magnetic field. The edges of the pole pieces where the scanning electron beam enters the influence of the magnetic field can be shaped to control the focal properties of the deflection magnet.

In operation, a focused electron beam is introduced to the deflection magnet assembly 70; the beam being focused in order to permit the use of a small gap between the poles 72 and 74 of the deflection magnet assembly to enhance its efficiency. When the electrons of the beam enter the field established between pole pieces 72 and 74, they execute circular orbits to emerge at the side of the chamber 76 at which the pipe 14 is located. With the deflection magnet assembly 70 oriented at 45° relative to the central axis of the electron beam, the electron beam will execute a turn of substantially 270° to emerge at substantially a right angle to its original direction. The rays of the electron beam exit deflection chamber 76 through pipe 14 and are introduced into the scanning member or device 86 in order to permit uniform irradiation of the internal surface of the tire 56 which is rotated relative to the deflection chamber for circumferential irradiation.

The deflection chamber and deflection magnet assembly are arranged co-axially with the tire 56 and, for use in irradiating other hollow objects, would similarly be disposed along an axis of symmetry of the object.

In each of the wide angle scanning apparatuses of the present invention, the scanning deflection device is disposed within the hollow object to be irradiated and the object is rotated about the scanning deflection device or the scanning deflection device is rotated within the object. Accordingly, the fixtures for supporting the objects to be irradiated are desirably designed to pick up the object to be irradiated, rotate the object about a central axis thereof and translate the rotating object by the scanning deflection device such that the scanning deflection device is disposed within the object. The fixture for supporting tires for irradiation by the scanning deflection device also will tilt the tire for proper positioning relative to the scanning deflection device assuming that the initial direction of the electron beam is either horizontal or vertical.

The scanning of the beam is desirably accomplished in a single plane to avoid striking the pole tips or coils of the scanning deflection device magnet, and the exact shape of the drive signal waveforms will depend on the configuration of the scanning deflection device magnet and the angular deflection scan range required for irradiating various regions of objects to be irradiated. The annular deflection scan range will vary with various applications, and the deflection scan can be produced on one or both sides of the beam axis.

Referring now specifically to FIGS. 10 to 16, there is illustrated in detail the construction of the beam scanning deflection device 20. The device 20 comprises, and reference is made initially to FIG. 10, a hollow, flat deflection chamber 90 and magnet assembly 92.

Figure 10:
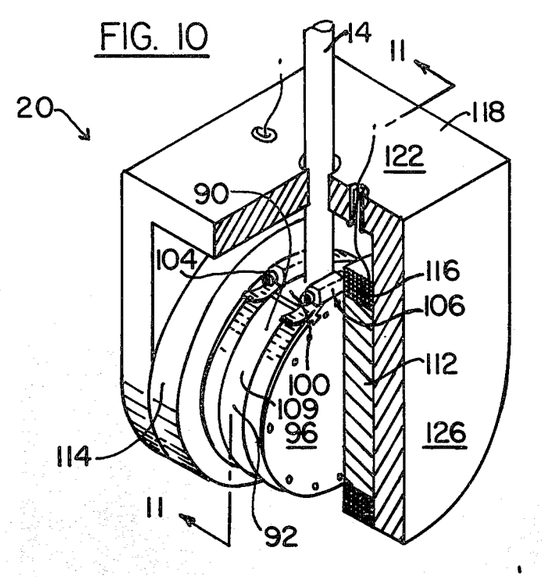
FIG. 10 is a detailed perspective view of the member 20 of FIG. 1.
Figure 11:
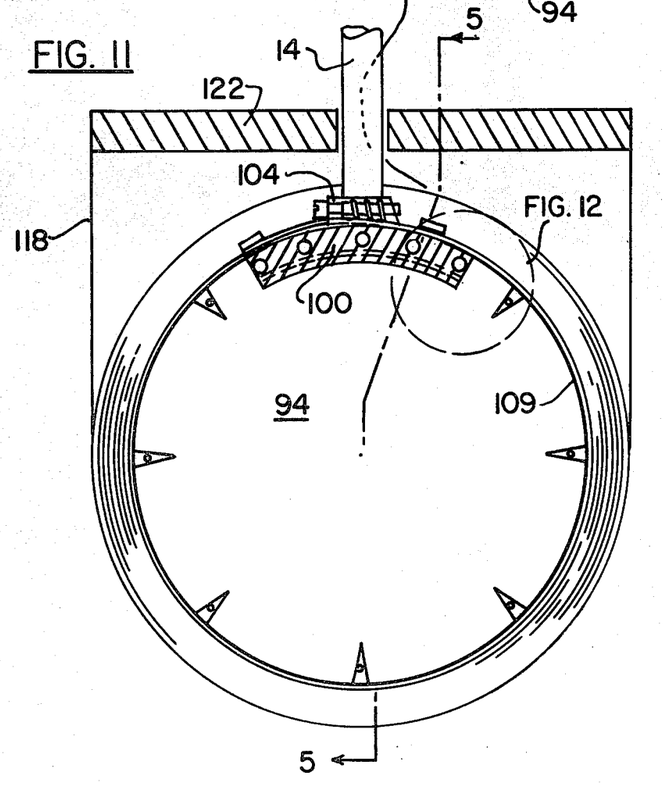
FIG. 11 is a section along line 11—11 of FIG. 10.
Figure 12:
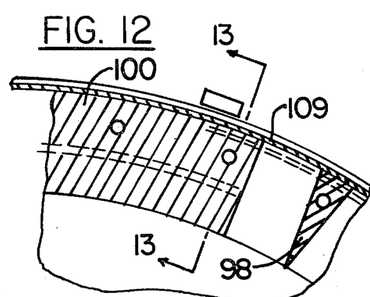
FIG. 12 is a sectional view of the part within the circle designated FIG. 12 in FIG. 11.
Figure 13:
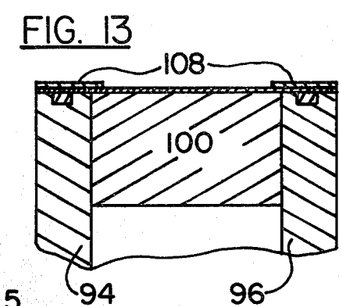
FIG. 13 is a section taken aong line 13—13 of FIG. 12.
Figures 14, 16:
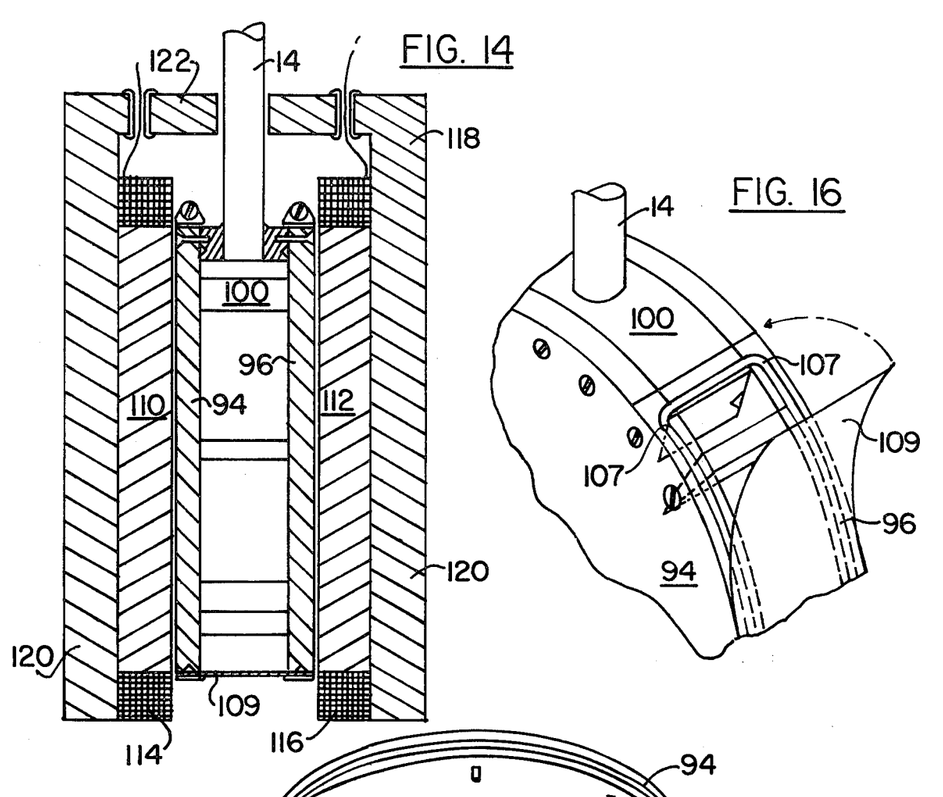
FIG. 14 is a detail view in section taken vertical along a plane through the center of the structure of FIG. 10.
FIG. 16 is a detailed view of the structure for reaching the chamber of FIG. 15.
Figure 15:
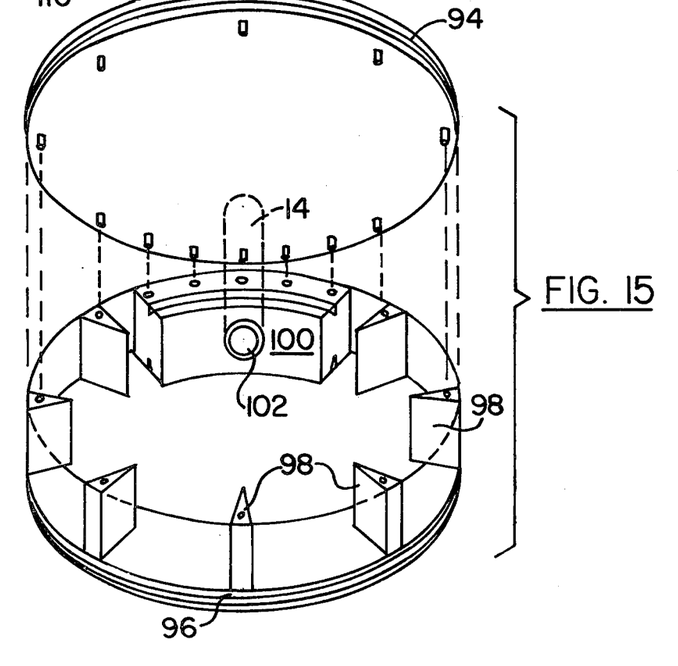
FIG. 15 illustrates the aligning pins located in the cover for closing the deflection chamber of FIG. 11.

The deflection chamber 90 comprises two flat circular discs 94 and 96 having spacing ribs 98 disposed between and equally spaced about the outer periphery only of the discs 94 and 96 for support; the ribs being bonded in place by suitable means such as welding. The ribs must withstand only compression forces of atmospheric pressure and thus tacking of the ribs should be sufficient.

An arcuate metal plate 100 is suitably secured (for example by braising) between the discs at their outer peripheries supplying the support between the discs 94 and 96 over a short arcuate region. The plate 100 receives the end of the vacuum pipe 14 in aperture 102 therein.

The space between the discs 94 and 96 is sealed by a foil window 109 which extends from one side of pipe 14 about the outer periphery of the edges of discs 94 and 96 to the other side of the pipe 14. The foil window is clamped against the edges of the discs by suitable clamps in the nature of pipe or hose clamps, pipe clamps 104 and 106 being illustrated in FIG. 10. In order to assure a proper seal, soft aluminum wire 107 is placed in a shallow groove 108 extending around the outer periphery of the edge of each of the discs 94 and 96 and lies between the foil and the discs. When the clamps 104 and 106 are drawn tight, the aluminum wire is mashed and seals the interface between the foil and the edges of the discs. Clamping bars 120 hold the foil against the wire 107 (see FIG. 16) where it comes over plate 100. Bars 120 are bolted to member 100.

The discs 94 and 96 should be fabricated of a strong material having a high electrical resistivity to reduce eddy current losses. Inconel is a suitable material and may be employed for the plate 100 also. The foil is preferably of titanium.

Referring now to the magnetic structure 92, flat circular discs 110 and 112 of high permeability magnetic material such as ferrite are disposed against the outer surfaces of the discs 94 and 96. Annular electric coils 114 and 116 are disposed about the circular edges of discs 110 and 112 and are excited by the generator 26 to establish a varying field extending across the chamber 20 whereby to cause the beam to sweep sequentially and successively from one end of foil window 109 to the other end thereof; approximately 270°.

A yoke 118 of magnetic material, such as ferrite, is employed to complete the magnetic path to provide a low external field. A large external field would produce some reverse bending of the electron beam and reduce its angular deflection.

The yoke 118 has two large faces 120 that are coextensive with discs 110 and 112 and coils 114 and 116. The faces are joined by a cross member 122 that extends transverse of the plane of the faces 120 and is apertured to accept the pipe 14.

Inasmuch as the present invention is subject to many variations, modifications and changes in detail, it is intended that all subject matter described above or shown in the accompanying drawings be interpreted as illustrative and not in a limiting sense.

What is claimed is:

1. Wide angle beam scanning apparatus for internally irradiating hollow objects with a beam of charged particles comprising
   particle accelerator means for producing a beam of charged particles; and
   scanning deflection means configured to be disposed within an object to be irradiated for receiving said beam along a beam axis and deflecting said beam from said beam axis to scan said beam through an angle of deflection greater than 90° from said axis whereby the inner surface of the object can be irradiated with charged particles.

2. Wide angle beam scanning apparatus as recited in claim 1 wherein said scanning deflection means is rotatable about said beam axis.

3. Wide angle beam scanning apparatus as recited in claim 1 and further comprising fixture means for supporting and rotating an object to be irradiated.

4. Wide angle beam scanning apparatus as recited in claim 1 and further comprising fixture means for moving an object to be irradiated in a direction along said beam axis.

5. Wide angle beam scanning apparatus as recited in claim 1 wherein said scanning deflection means includes generator means supplying a drive signal and a beam scanning device operable in response to said drive signal to deflect said beam from an initial angle of deflection greater than 90° on one side of said beam axis through a position in alignment with said axis to an angle of deflection greater than 90° on the opposite side of said beam axis.

6. Wide angle beam scanning apparatus as recited in claim 5 wherein said drive signal has shallow slope portions to cause said beam to be deflected at an angular rate slower at corner regions of an object to be irradiated than at sides of an object to be irradiated.

7. Wide angle beam scanning apparatus as recited in claim 1 wherein said scanning deflection means includes generator means supplying a drive signal and a beam scanning device operable in response to said drive signal, said drive signal causing said beam to be deflected to scan from an angle relative to said beam axis of from substantially 45° to substantially 135°.

8. Wide angle beam scanning apparatus as recited in claim 1 wherein said scanning deflection means includes generator means supplying a drive signal and a beam scanning device operable in response to said drive signal, said drive signal causing said beam to be deflected to scan from an angle relative to said axis of substantially 135° on opposite sides of said axis.

9. Wide angle beam scanning apparatus as recited in claim 1 wherein said scanning deflection means scans said beam through an angle of deflection greater than 90° on opposite sides of said axis.

10. Wide angle beam scanning apparatus as recited in claim 9 wherein the object to be irradiated has a hollow toroidal configuration and further comprising deflection magnet means for deflecting said beam to coincide with said beam axis.

11. Wide angle beam scanning apparatus as recited in claim 10 and further comprising means for rotating said object about a central axis of rotation thereof.

12. Wide angle beam scanning apparatus as recited in claim 10 wherein said deflection magnet means includes quadrupole magnetic lenses.

13. Wide angle beam scanning apparatus as recited in claim 11 wherein said deflection magnet means is disposed along said central axis of rotation.

14. Wide angle beam scanning apparatus as recited in claim 13 wherein said beam is supplied along said central axis of rotation and said deflection magnet means deflects said beam to coincide with said beam axis.

15. Wide angle beam scanning apparatus as recited in claim 13 wherein said beam is supplied at an angle to said central axis of rotation and said deflection magnet means deflects said beam to coincide with said beam axis.

16. A method of internally irradiating hollow objects with a beam of charged particles comprising the steps of
   disposing a beam scanning deflection device within an object to be irradiated; and
   operating the beam scanning deflection device to scan the beam over an angle relative to a beam axis along which the beam is received by the beam scanning deflection device to irradiate a swath of an object to be irradiated.

17. The method as recited in claim 16 wherein said beam scanning deflection device operating step includes scanning the beam over an angle relative to the beam axis greater than 90° on opposite sides of the beam axis.

18. The method as recited in claim 16 wherein said beam scanning deflection device operating step includes scanning the beam over an angle relative to the beam axis greater than 90° and not coinciding with the beam axis.

19. The method as recited in claim 17 wherein said beam scanning deflection device operating step includes scanning the beam through an angle relative to the beam axis of substantially 135° to substantially 45°.

20. The method as recited in claim 18 wherein said beam scanning deflection device operating step includes scanning the beam on opposite sides of the beam axis.

* * * * *